(12) United States Patent
Fares et al.

(10) Patent No.: US 9,517,193 B2
(45) Date of Patent: Dec. 13, 2016

(54) ANTIPERSPIRANT/DEODORANT COMPOSITIONS

(71) Applicant: ISP INVESTMENTS INC., Wilmington, DE (US)

(72) Inventors: Hani M. Fares, Somerset, NJ (US); Donald I. Prettypaul, Englewood, NJ (US)

(73) Assignee: ISP INVESTMENT LLC, Wilmington, DE (US)

( * ) Notice: Subject to any disclaimer, the term of this patent is extended or adjusted under 35 U.S.C. 154(b) by 0 days.

(21) Appl. No.: 14/349,521

(22) PCT Filed: Oct. 2, 2012

(86) PCT No.: PCT/US2012/058416
§ 371 (c)(1),
(2) Date: Apr. 3, 2014

(87) PCT Pub. No.: WO2013/052454
PCT Pub. Date: Apr. 11, 2013

(65) Prior Publication Data
US 2014/0242015 A1    Aug. 28, 2014

Related U.S. Application Data

(60) Provisional application No. 61/542,880, filed on Oct. 4, 2011.

(51) Int. Cl.
| | |
|---|---|
| *A61K 8/81* | (2006.01) |
| *A61Q 15/00* | (2006.01) |
| *A61K 8/19* | (2006.01) |
| *A61K 8/86* | (2006.01) |
| *A61K 8/88* | (2006.01) |
| *A61K 8/27* | (2006.01) |

(52) U.S. Cl.
CPC ............... *A61K 8/8164* (2013.01); *A61K 8/19* (2013.01); *A61K 8/27* (2013.01); *A61K 8/86* (2013.01); *A61K 8/88* (2013.01); *A61Q 15/00* (2013.01); *A61K 2800/30* (2013.01)

(58) Field of Classification Search
None
See application file for complete search history.

(56) References Cited

U.S. PATENT DOCUMENTS

| | | | |
|---|---|---|---|
| 4,275,054 A | 6/1981 | Sebag et al. | |
| 5,176,898 A * | 1/1993 | Goldberg | A61K 8/585 424/47 |
| 6,190,645 B1 * | 2/2001 | SaNogueira | A61K 8/35 424/400 |
| 6,517,823 B1 * | 2/2003 | Norman | A61K 8/39 424/400 |
| 2002/0119108 A1 | 8/2002 | Rieley et al. | |
| 2005/0100521 A1 | 5/2005 | Cropper | |
| 2006/0051306 A1 | 3/2006 | Brown et al. | |
| 2010/0297201 A1 | 11/2010 | Gillece et al. | |

FOREIGN PATENT DOCUMENTS

WO    WO 2009/091794    *   7/2009 ............... A61K 8/00

OTHER PUBLICATIONS

International Search Report of PCT/US2012/058416 published on Apr. 11, 2013.

* cited by examiner

*Primary Examiner* — Bethany Barham
*Assistant Examiner* — Barbara Frazier
(74) *Attorney, Agent, or Firm* — William J. Davis

(57) ABSTRACT

Antiperspirant/deodorant compositions have lower, or even zero amounts of aluminum and/or zirconium antiperspirant actives. A polymer having one or more anhydride and/or diacid moieties, such as succinic (maleic) anhydride and/or diacid. The antiperspirant/deodorant compositions comprise a polymer with a non-zero acid value and a cationic species, which may be a cationic polymer, cationic molecule, cation, and/or a cationic carrier. Product are formed for the antiperspirant/deodorant composition, as well as a method of treating perspiration.

5 Claims, No Drawings

ANTIPERSPIRANT/DEODORANT COMPOSITIONS

CROSS REFERENCE TO RELATED APPLICATIONS

This application is the national stage of PCT Application No. PCT/US2012/058416 filed Oct. 2, 2012, which claims priority from Provisional Patent Application No. 61/542,880, filed Oct. 4, 2011, the entire disclosures of which are hereby incorporated in their entirety.

FIELD OF THE INVENTION

Provided herein are antiperspirant/deodorant compositions and methods of reducing perspiration and/or odor. More particularly, the present teachings relate to new and improved antiperspirant/deodorant compositions that provide a reduced level of aluminium and/or zirconium, or even no aluminium and/or zirconium, compared to known antiperspirant/deodorants.

BACKGROUND OF THE INVENTION

Antiperspirant products typically use aluminum- and zirconium-based salts as the active antiperspirant ingredient to control perspiration and malodor. However, many consumers may hold a negative view of their use due to health and environmental concerns. Moreover, the high concentrations of the active antiperspirant ingredients can cause irreversible staining of clothing.

The above issues have been addressed in a number of ways. One approach is the addition of one or more water-soluble polymers containing Brønsted acid groups in combination with aluminium and/or zirconium salts to the antiperspirant/deodorant composition. See, e.g., U.S. Pat. No. 6,616,921; U.S. Patent Application 2005/0100521; and International Application WO 02/49590. However, in the only issued patent, the water soluble polymers are described to form true solutions in water, where a true solution typically has an absorbance of less than 0.2, preferably less than 0.1 (for a 1 cm path length at 600 nm). Also related is pending U.S. Provisional Application 61/450,303, which teaches antiperspirant/deodorant compositions having a reduced concentration of antiperspirant active while effectively controlling perspiration and malodor. The contents of the '921 patent, the '521 and '590 patent applications, and the provisional application are hereby incorporated in their entirety by reference.

A homeopathic approach eliminates aluminium- and zirconium-based salts in favor of antiperspirant actives from plant origin, such as *salvia officinalis* oil. While these alternative compositions have met with mixed success, they are generally regarded to be much less effective in controlling perspiration than conventional compositions. Another solution to the problem is to abandon perspiration control, and instead address malodor that can arise from the perspiration, for example, by using baking soda products. However, homeopathic responses are not adequate for many people, who must reduce or eliminate perspiration using more effective means because their preferences and/or lifestyles do not permit uncontrolled sweating, or for other reasons.

Despite the concurrent advancements in antiperspirant technology, effective antiperspirant/deodorant compositions having a significantly reduced, or even a zero level of aluminium- and/or zirconium-based salts are not known, but would be enthusiastically adopted by consumers.

Accordingly, there is a need for new antiperspirant/deodorant compositions that can reduce the high concentrations of conventional antiperspirant and deodorant ingredients while maintaining antiperspirant/deodorant efficacy.

SUMMARY

In one aspect the invention provides antiperspirant/deodorant compositions having lower, or even zero amounts, of antiperspirant actives based on aluminium cations or zirconium cations. In a first embodiment, the compositions comprise a polymer having one or more anhydride moieties, such as a polymer with succinic anhydride moieties, and/or diacid moieties, such as maleic acid. A second embodiment provides antiperspirant/deodorant compositions comprising a polymer with a non-zero acid value and a cationic species. The cationic species may be a cationic polymer, cationic molecule, cation, and/or a cationic carrier.

Also provided are product forms for the antiperspirant/deodorant composition, as well as a method of treating perspiration.

DETAILED DESCRIPTION

In one embodiment, the antiperspirant/deodorant compositions comprise at least one polymer having at least one anhydride moiety and/or at least one diacid moiety, wherein the compositions are essentially free of aluminium cations and zirconium cations. The antiperspirant/deodorant compositions may comprise at least one polymer having an anhydride moiety and no aluminium cations and no zirconium cations.

By a second embodiment, the antiperspirant/deodorant compositions comprise at least: (A) a polymer with a non-zero acid value, and (B) one or more cationic species, which may be one or more cationic polymer(s), cationic molecule(s), cation(s), and/or cationic carrier(s). As with the first embodiment, compositions by the second embodiment are essentially free of aluminium cations and zirconium cations. In this effect, the compositions are essentially free of aluminium salts and zirconium salts. As a separate distinction within this second embodiment are antiperspirant/deodorant compositions contain no aluminium cations and no zirconium cations.

Before proceeding to a detailed description of these embodiment, a few terms will be explained.

For compositions described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited process steps.

Where an element or component is said to be included in and/or selected from a list of recited elements or components, it should be understood that the element or component can be anyone of the recited elements or components, or can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes", "including," "have," "has," "having," "contain," "contains," or "containing" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "alkyl" refers to a straight-chain or branched saturated hydrocarbon group. Examples of alkyl groups include methyl, ethyl, propyl (e.g., n-propyl and iso-propyl), butyl (e.g., n-butyl, iso-butyl, sec-butyl, tert-butyl), pentyl (e.g., n-pentyl, iso-pentyl, neopentyl), hexyl groups, and the like. In various embodiments, an alkyl group can have 1 to 40 carbon atoms (i.e., C1-C40 alkyl group), for example, 1-20 carbon atoms (i.e., C1-C20 alkyl group). In some embodiments, an alkyl group can have 1 to 6 carbon atoms, and can be referred to as a "lower alkyl group." Examples of lower alkyl groups include methyl, ethyl, propyl (e.g., n-propyl and isopropyl), butyl (e.g., n-butyl, iso-butyl, sec-butyl, tert-butyl), pentyl (e.g., n-pentyl, iso-pentyl, neopentyl), and hexyl groups.

At various places in the present specification, substituents are disclosed in groups or in ranges. It is specifically intended that the description include each and every individual sub combination of the members of such groups and ranges. For example, the term "C1-C6 alkyl" is specifically intended to individually disclose C1, C2, C3, C4, Cs, C6, C1-C6, C1-C5, C1-C4, C1-C3, C1-C2, C2-C6, C2-CS, C2-C4, C2-C3, C3-C6, C3-CS, C3-C4, C4-C6, C4-CS, and C5-C6 alkyl. By way of other examples, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20.

The term "alkaline earth metal" refers to beryllium, magnesium, calcium, strontium, barium, and radium.

The term "alkali metal" refers to lithium, sodium, potassium, rubidium, cesium, and francium.

The term "polymer" refers to a molecule including a plurality of one or more repeat units or monomers connected by covalent chemical bonds. A polymer can be represented by the general formula:

wherein M is a repeat unit or monomer. The degree of polymerization can range from 2 to greater than 10,000. The polymer may have only one type of repeat unit (i.e., a homopolymer), or may comprising more than one type of repeat unit (i.e., a non-homopolymer). Examples of non-homopolymers include those polymerized from two repeat units, three repeat units, and even more. The polymer can be linear or branched. Unless specified otherwise, the assembly of the repeat units in non-homopolymers can be head-to-tail, head-to-head, or tail-to-tail. In addition, unless specified otherwise, non-homopolymers can present the repeat unit in a random, alternating, or block structure.

Branched polymers can include dendritic polymers, such as dendronized polymers, hyperbranched polymers, brush polymers (also called bottle-brushes), and the like. For clarity, the term "branched" refers to any and all of these categories.

A polymer has at least one "backbone" or a "backbone chain," which is a series of covalently bonded atoms that together form a nearly continuous chain of atoms connecting the repeat units or monomers used to form the polymer. A "pendant group" or a "side chain" of a polymer is a group not part of the backbone chain to which is it pendant (but may be part of a second backbone). Pendant groups may contain functional groups or moieties that can facilitate the polymerization reaction, for example, formation of the polymer backbone. Pendant groups also can be selected to be beneficial after polymerization, for example, influencing the properties and characteristics of the resulting polymer.

The term "(meth)acrylate" refers to acrylate and methacrylate. Other uses of "(meth)" follow suit [e.g., "(meth) acrylamide" refers to acrylamide and methacrylamide].

The term "antiperspirant/deodorant composition" refers to any composition that reduces perspiration. The term "antiperspirant/deodorant composition" includes compositions that reduce perspiration, as well as those compositions that reduce perspiration and any malodor associated with perspiration (e.g., due to bacterial growth).

The Antiperspirant and Antiperspirant/Deodorant Compositions

Effective antiperspirant/deodorant compositions have been discovered that relieve the formulary burden of high concentrations of aluminium cations and/or zirconium cations. Both embodiments of the invention are described in that they are essentially free of aluminium cations and/or zirconium cations. Within the context of the invention, the term "essentially free" refers to a concentration of aluminium cations and/or zirconium cations such that a similar composition without the anhydride-containing polymer (as in the first embodiment) or the polymer with a non-zero acid value (as in the second embodiment) does not provide antiperspirant efficacy as defined by the U.S. Food and Drug Administration. Thus, the term "essentially free" is not restricted to mean "zero" or "almost zero" aluminium cations or zirconium cations, although these concepts are included in what is meant. More broadly, "essentially free" refers to a level of aluminium cations and/or zirconium cations in a similar compositions without the aforementioned polymers such that a 20% reduction in sweat production in about 50% of a given population is not attained. To illustrate this concept, consider a composition containing 3% aluminium cations and/or zirconium cations and no aforementioned polymer. If that composition does not provide at least a 20% reduction in sweat production in about 50% of a given population, then that composition is considered to be "essentially free" of aluminium cations and/or zirconium cations. Of course, analogous compositions with less than 3% aluminium cations and/or zirconium cations also are considered to be "essentially free" of those cations.

Contrary to expectations, it has been discovered that antiperspirant/deodorant compositions can effectively control perspiration without exposing the user to levels of aluminium cations or zirconium cations found in commercial products. As introduced earlier, there are two embodiments to the invention.

By a first embodiment, the antiperspirant/deodorant composition comprises one or more polymers having at least one anhydride moiety or a diacid moiety. The anhydride moiety may be any known in the art, such as succinic (maleic) anhydride, itaconic anhydride, citraconic anhydride, or combinations thereof. The anhydride moiety(ies) may occur along the polymer backbone, or be pendant to it. The diacid moiety may result from the hydrolysis of one or more anhydride moieties, as in the conversion of a succinic (maleic) anhydride moiety to a succinic (maleic) diacid moiety.

The chemistry of this polymer comprising anhydride moieties and/or diacid moieties may be designed by one skilled in the art to enhance the antiperspirant/deodorant compositions, for example, film formation, substantivity, and/or water resistance. As such, it may be desirable to polymerize a first monomer having anhydride moieties with one or more additional monomers, in other words, the polymer may be a non-homopolymer. By way of example, the one or more other monomer(s) may be selected from among (meth)acrylamides, (meth)acrylates, olefins, allyls, cinnamyls, fumarates, maleates, maleimides $\alpha,\beta$-olefinically unsaturated carboxylic nitriles, styrenes, vinyl esters, vinyl acetates, vinyl amides, vinyl alcohols, vinyl carbonates, vinyl carbamates, vinyl thiocarbamates, vinyl ureas, vinyl ethers, vinyl halides, vinyl imidazoles, vinyl lactams, vinyl pyridines, vinyl silanes, vinyl sulfones, benzoxazines, epoxies, oxazolines, oxetanes, and combinations thereof.

Specific examples of suitable polymers having anhydride moiety include, but are not limited to methyl vinyl ether/maleic anhydride copolymer, such as Gantrez® AN sold by Ashland Specialty Ingredients. A product review of this polymer is given in the brochure *Polymers For Oral Care* (Ashland Specialty Ingredients, July 2003), which is incorporated in its entirety by reference. A second polymer related to the first is methyl vinyl ether/maleic anhydride copolymer crosslinked with decadiene, which is provided by Ashland Specialty Ingredients under the name AP-1. A third example is isobutylene/maleic anhydride copolymer, such as I-Rez® 160, which also is sold by Ashland Specialty Ingredients. Also suitable are crosslinked PVM/MA copolymers such as a described in U.S. Pat. No. 5,202,112. These crosslinked PVM/MA copolymers have in a 1% (w/w) aqueous solution an elastic modulus (G') with a minimum value of 1,000 dynes/cm$^2$ and a value of tan $\delta$ ranging from more than 0.05 to less than 1. The '112 patent is incorporated in its entirety by reference.

Additional examples include methyl vinyl ether/maleic acid copolymer (e.g., Gantrez® S-95 and Gantrez® S-97 sold by Ashland Specialty Ingredients).

These products also point out a nomenclature peculiarity that exists with polymers polymerized from maleic anhydride. After polymerization the maleic anhydride moiety forms a succinic anhydride moiety, and, as such these polymers might be called succinic anhydride copolymers. In order to avoid any confusion, the term "succinic (maleic) anhydride" will be used when naming the maleic anhydride moiety after its polymerization.

One skilled in the art recognizes that the anhydride-containing polymers are examples of Brønsted acid polymers. By definition, Brønsted acid polymers are those polymers capable of losing ("donating") a proton (i.e., H$^+$). Without being bound by theory, it appears that an composition comprising a Brønsted acid polymer that is essentially free of aluminium cations and zirconium cations exhibits effective antiperspirant/deodorant activity. A review of Brønsted acid polymers is given in U.S. Pat. No. 6,616,921; U.S. Patent Application 2005/0100521, and in international application WO 02/49590. Suitable Brønsted acid polymers according to the present invention include those polymers having a maleic acid moiety, carboxylic acid moiety, sulfonic acid moiety, phosphonic acid moiety, and anhydride moiety that is at least partially hydrolyzed. Thus, the invention contemplates the use of these Brønsted acid polymers in this first embodiment.

Maleic anhydride non-homopolymers based on two different repeat units (i.e., maleic anhydride and a second monomer) typically polymerize in 50:50 molar ratios [e.g., 50 mole percent succinic (maleic) anhydride:50 mole percent second monomer]. If a higher anhydride content is desired in the antiperspirant/deodorant composition, then a blend may be prepared of the first non-homopolymer with a homopolymer of maleic anhydride. Such homopolymers are taught by U.S. Pat. No. 3,186,972 and GB Patents 1,073,323 and U.S. Pat. No. 1,120,789, all of which are hereby incorporated in their entirety by reference. Analogously, if a lower concentration is needed, then maleic anhydride may be polymerized with a second and a third monomer, where the second and third monomers can be selected to tailor the properties of the resulting terpolymer. Optionally, lower anhydride concentrations can be produced by lowering the concentration of the anhydride-containing polymer in the antiperspirant/deodorant composition.

The molecular weight of the anhydride-containing polymer is not restricted, provided the antiperspirant/deodorant composition is effective in reducing perspiration compared to a placebo control (i.e., no treatment). Usually, this polymer's molecular weight is chosen based on product manufacturing, delivery/application, and efficacy considerations. Lower polymer molecular weight may be suitable for liquid and liquid-like product forms, where are higher molecular weight may be useful for solid and solid-like product forms. In general, the polymers may have a molecular weight of about 1,000 Da to about 5,000,000. Particular aspects of the invention may employ a polymer having a molecular weight from about 10,000 Da to about 2,000,000 Da. For example, Gantrez® AN is available in a wide range of weight-average molecular weight, ranging from about 200,000 Da (Gantrez® AN-119) to about 2,000,000 Da (Gantrez® AN-169). Gantrez® S-95 has an average weight-average molecular weight of about 216,000 Da, while Gantrez® S-97 has an average weight-average molecular weight of about 1,500,000 Da.

The addition level of polymer having at least one anhydride moiety is not particularly limited, inasmuch as the antiperspirant/deodorant composition effectively reduces perspiration compared to a placebo control. In general, the polymer addition amount may range from about 0.1% to about 15%, more particularly from about 0.5% to about 5%, and even more particularly from about 1% to 3%, all of which are based on the total weight of the antiperspirant/deodorant composition. It is understood by one skilled in the art that an effect amount of the polymer typically depends on the types and amounts of other ingredients in the final antiperspirant/deodorant composition.

The invention further embraces a second embodiment for antiperspirant/deodorant compositions which comprise at least: (A) a polymer with a non-zero acid value, and (B) one or more cationic species. As with the first embodiment, compositions by the second embodiment are essentially free of aluminium cations and zirconium cations. In this effect, the compositions are essentially free of aluminium salts and zirconium salts. As a separate distinction within this second embodiment, antiperspirant/deodorant compositions are provided that contain no aluminium cations and no zirconium cations.

The first ingredient in the second embodiment is (A) a polymer having a non-zero acid value. Generally speaking, acid value is a measure of how much base is required to neutralize an acid compound. A base, such as potassium hydroxide or sodium hydroxide, typically is added using a titration method, such as potentiometric titration. The acid value is then reported as:

$$\text{acid value} = \frac{V \times N \times MW_{base}}{Wt}$$

wherein V is the volume of base required for neutralization (in mL), N is the normality of the base solution (in eq./L), $MW_{base}$ is the molecular weight of the base (in g/mol), and Wt is the weight of the sample (in g). When calculated as such, acid value bears the units of mg base per 1 g of sample.

Polymers having a non-zero acid value typically are those polymers having one or more of the following moieties: an anhydride moiety, or an acid moiety such as a maleic acid moiety, a half ester of a maleic acid moiety, a carboxylic acid moiety, a phosphoric acid moiety, or a sulfonic acid moiety. Such a moiety may be native to the monomer prior to polymerization (e.g., acrylic acid), may be converted after polymerization (e.g., anhydrides, also described later), or may be added to the polymer through one or more reactions (e.g., graft reactions to create pendant acid-contributing moieties).

These polymers may have any content of these moieties provided that the polymer have a non-zero acid value. More particularly, the polymer has an acid value greater than about 150, greater than about 200, greater than about 250, greater than about 300, greater than about 500, or even greater than about 700 or about 800.

The description of acid-contributing polymer moieties includes anhydrides, which includes succinic (maleic) anhydride, itaconic anhydride, and citraconic anhydride. The diacid forms of these anhydrides are succinic (maleic) diacid, itaconic diacid, and citraconic diacid. One skilled in the art recognizes that anhydrides are predicted to have a zero acid value, which would be true if each and every anhydride moiety is completely unhydrolyzed. However, anhydrides must be included in this list of moieties that contribute to a non-zero acid value. First, it is impossible to prescribe that each and every anhydride moiety will remain intact and unhydrolyzed, as even minute amounts of hydrolysis (e.g., humidity in the air or residual water content in an otherwise "anhydrous" formula) will result in a non-zero acid value. A level of hydrolyzed "impurity" in the anhydride polymer is sufficient to be useful in the invention. Second, it is appreciated that latent acid groups, like anhydrides, readily hydrolyze to their diacid form. It is in these regards that anhydrides perform like acid moieties in the invention.

Also suitable are polymers having an acetylacetone moiety, which is a moiety forming enol and keto tautomers in solution:

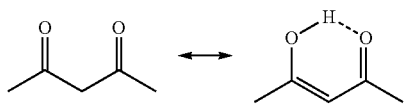

An acetylacetone moiety may reside in a polymerizable monomer, such as acetoacetoxyethyl(meth)acrylate:

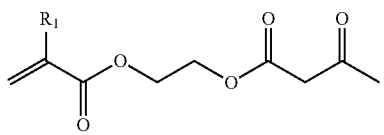

wherein $R_1$ is hydrogen or methyl. Acetoacetoxyethyl methacrylate is sold by The Eastman Chemical Company under the trade name AAEM.

The polymer having a non-zero acid value may be a homopolymer. For example, homopolymers based on monomers having an anhydride or acid moiety may be used. Non-limiting examples of acid moieties include maleic acid moiety, a half ester of a maleic acid moiety, a carboxylic acid moiety, a phosphoric acid moiety, or a sulfonic acid moiety. Specific examples of such polymers include the following: poly(acrylic acid) and partially crosslinked and/or branched poly(acrylic acid) (i.e. Carbopol® 940 sold by The Lubrizol Corporation), and polymethacrylic acid. Also suitable are the homopolymers of maleic anhydride, such as the polymers taught by U.S. Pat. No. 3,186,972 and GB Patents 1,073,323 and U.S. Pat. No. 1,120,789. Alkaline earth metal salts, alkali metal salts, and/or ammonium salts of these homopolymers also may be used. The homopolymer may have a weight-average molecular weight from about 2,000 Da to about 5,000,000 Da, more particularly from about 5,000 Da to about 3,000,000 Da, and even more particularly from about 10,000 Da to about 2,000,000 Da.

The polymer having a non-zero acid value also may be a non-homopolymer. Non-homopolymers may offer advantages to the formulation scientist in designing the antiperspirant/deodorant compositions, since the addition of one or more other monomers can help modulate any number of properties, such as processability, aesthetics, antiperspiration performance, and/or deodorant performance. The optional one or more comonomers for the polymerization may be selected from (meth)acrylamides, (meth)acrylates, olefins, allyls, cinnamyls, fumarates, maleates, maleimides α,β-olefinically unsaturated carboxylic nitriles, styrenes, vinyl esters, vinyl acetates, vinyl amides, vinyl alcohols, vinyl carbonates, vinyl carbamates, vinyl thiocarbamates, vinyl ureas, vinyl ethers, vinyl halides, vinyl imidazoles, vinyl lactams, vinyl pyridines, vinyl silanes, vinyl sulfones, benzoxazines, epoxies, oxazolines, and oxetanes. The addition of one or more comonomers may be used to create non-homopolymers having two repeat units, three repeat units, or even more.

The non-homopolymer may have a weight-average molecular weight from about 2,000 Da to about 5,000,000 Da, more particularly from about 5,000 Da to about 3,000, 000 Da, and even more particularly from about 10,000 Da to about 2,000,000 Da.

In general, the non-homopolymer may comprise from about 0.5 molar percent acid content to about 99.5 molar percent of the acid monomer (or monomer converted to acid functionality), the balance of the polymer being one or more other comonomer(s). More particularly, the non-homopolymer may comprise from about 2 molar percent to about 98 molar percent of the acid monomer (or monomer converted to acid functionality), and even more particularly from about 5 molar percent to about 95 molar percent of the acid monomer. One skilled in the art appreciates that this range in monomer amounts depends on the types and amounts of comonomer(s) and the formulation of the antiperspirant/deodorant composition.

Maleic anhydride non-homopolymers based on two different repeat units typically polymerize in 50:50 molar ratios [e.g., 50 mole percent methyl vinyl ether:50 mole percent succinic (maleic) anhydride]. If a higher anhydride content is desired in the antiperspirant/deodorant composition, then a blend may be prepared of the first non-homopolymer with a homopolymer of maleic anhydride.

The homopolymers and non-homopolymers described herein may be functionalized to produce polymers that also may be used. For example, if latent acid groups (such as anhydrides) are present after polymerization, a portion of the latent acid groups can be hydrolyzed to increase the acid value of the polymer. In addition, a polymer derived from, in part, maleic anhydride, can be functionalized, e.g., with an alkyl amine such as butylamine, octylamine or dodecylamine, to produce an amic acid or an imide, incorporating the alkyl group into the polymer and thereby increasing its hydrophobicity.

More particularly, suitable non-homopolymers having a non-zero acid value include the following polymers: calcium/sodium PVM/MA copolymer (Gantrez® MS-955); PVM/MA copolymer (Gantrez® S-95 and Gantrez® S-97); PVM/MA decadiene crosspolymer (Stabileze® QM); ethyl ester of PVM/MA copolymer (Gantrez® SP-215, Gantrez® ES-215); n-butyl ester of PVM/MA copolymer (Gantrez® A-425, Gantrez® ES-425, Gantrez® ES-435); iso-propyl ester of PVM/MA copolymer (Gantrez® ES-335); acrylic acid/VP crosspolymer (UltraThix™ P-100); sodium polyacrylate (and) hydrogenated polydecene (and) trideceth-6 crosslinked polymer (RapiThix® A-60); acrylates/beheneth-25 methacrylate copolymer (Aculyn® 28); isobutylene/maleic anhydride copolymer (I-Rez® 160); acrylates/C10-30 alkyl acrylate crosspolymer; acrylates/ceteth-20 itaconate copolymer; acrylates/ceteth-20 methacrylate copolymer; acrylates/dimethicone copolymer; acrylates/dimethylaminoethyl methacrylate copolymer; acrylates/ethylhexyl acrylate copolymer; acrylates/ethylhexylacrylamide copolymer; acrylates/steareth-20 methacrylate copolymer; acrylates/steareth-20 itaconate copolymer; acrylic acid/acrylonitrogens copolymer; adipic acid/diethylene glycol/glycerin crosspolymer; adipic acid/diethylenetriamine copolymer; dipic acid/dimethylaminohydroxypropyl diethylenetriamine copolymer; adipic acid/epoxypropyl diethylenetriamine copolymer; adipic acid/isothphalic acid/neopentyl glycol/trimethylolpropane copolymer; adipic acid/neopentyl glycol/trimellitic anhydride copolymer; AMP-acrylates/diacetoneacrylamide copolymer; AMP-acrylates/dimethylaminoethyl methacrylate copolymer; benzoic acid/phthalic anhydride/pentaerythritol/neopentyl glycol/palmitic acid copolymer; butyl benzoic acid/phthalic anhydride/trimethylolethane copolymer; DMAPA acrylates/acrylic acid/acrylonitrogens copolymer; ethylene/acrylic acid copolymer; ethylene/acrylic acid/VA copolymer; ethylene/maleic anhydride copolymer; phthalic anhydride/adipic acid/castor oil/neopentyl glycol/PEG-3/trimethylolpropane copolymer; phthalic anhydride/benzoic acid/trimethylolpropane copolymer; phthalic anhydride/butyl benzoic acid/propylene glycol copolymer; phthalic anhydride/glycerin/glycidyl decanoate copolymer; phthalic anhydride/trimellitic anhydride/glycols copolymer; PVP/VA/itaconic acid copolymer; rosin acrylate (rosin reaction products with acrylic acid); sodium C4-12 olefin/maleic acid copolymer; sodium tauride acrylates/acrylic acid/acrylonitrogens copolymer; trimethylpentanediol/isophthalic acid/trimellitic anhydride copolymer; and combinations thereof.

As suggested in the above list, a polymer having a non-zero acid value may be completely linear, completely crosslinked such that it is water swellable but water insoluble (e.g., zero recovery from a gel permeation chromatography pre-filter), or partially crosslinked and/or partially branched (e.g., some recovery from a gel permeation chromatography). Indeed, a slightly crosslinked or a branched polymer may enhance the performance of the antiperspirant/deodorant composition by allowing the use of higher molecular weight polymers for product formulation and delivery, or skin substantivity. Combinations can be used of non-crosslinked, crosslinked, lightly crosslinked, and branched polymers.

In addition to the polymer having a non-zero acid value, the second embodiment of the invention also comprises (B) one or more cationic species, for which there are at least four choices: a cationic polymer, a cationic molecule, a cation, or a cationic carrier. Combinations of these cationic species may be used. The paragraphs that follow describe various aspects of this (B) cationic species.

First, the cationic species may be a cationic polymer. This concept of "cationic polymer" includes any polymer containing cationic groups, pseudo-cationic, and/or groups which may be ionized into cationic groups. Within this group of cationic polymers are the "pseudo-cationic polymers," which do not possesses an inherent positive charge, but do possess behavior similar to cationic polymers. Pseudo-cationicity arises in these polymers due to electron donating or electron receiving atoms and/or groups within the polymer. For example, included among pseudo-cationic polymers are those polymers having a lactam group (such as pyrrolidone, piperidone, and caprolactam), especially in acid conditions. (One skilled in the art recognizes that the pH of skin is typically slightly acidic, having a pH from about 4.2 to about 5.6.) The electron pair of the amide group forming a pseudo-cationic nitrogen center:

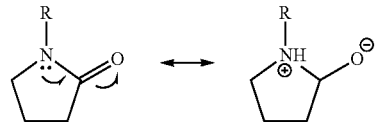

wherein R is any substituent to the lactam nitrogen.

Cationic polymers include those polymer comprising primary, secondary, tertiary and/or quaternary amine groups which may either form part of the main polymer chain or may be side substituents linked to the main chain. Suitable cationic polymers can be found in the *International Cosmetic Ingredient Dictionary* (7th ed., 1997). For example, the organic cationic polymer may contain cationic nitrogen-containing moieties such as quaternary ammonium or cationic protonated amino moieties. The cationic protonated amines can be primary, secondary, or tertiary amines, depending upon the particular species and the selected pH of the composition.

The weight-average molecular weight of the cationic polymer may range from about 1,000 Da to about 5,000,000 Da, and particularly ranges from 5,000 Da to about 3,000,000 Da.

Any anionic counterions can be used in association with the cationic polymers so long as the counterions do not otherwise unduly impair product performance, stability or aesthetics. Non limiting examples of such counterions include halides (e.g., chlorine, fluorine, bromine, iodine), sulfate, and methylsulfate.

The cationic nitrogen-containing moiety of the cationic polymer may be present as a substituent on all or on some of the monomer units thereof. Thus, the cationic polymer includes homopolymers and non-homopolymers (which includes copolymers, terpolymers, and so forth) of quaternary ammonium or cationic amine-substituted monomer units, optionally in combination with other monomers. These other monomers that can be used to create non-homopolymers may be one or more of the following: (meth)acrylamides, (meth)acrylates, olefins, allyls, cinnamyls, fumarates, maleates, maleimides, α,β-olefinically unsaturated carboxylic nitriles, styrenes, vinyl esters, vinyl acetates, vinyl amides, vinyl alcohols, vinyl carbonates, vinyl carbamates, vinyl thiocarbamates, vinyl ureas, vinyl ethers, vinyl halides, vinyl imidazoles, vinyl lactams, vinyl pyridines, vinyl silanes, vinyl sulfones, benzoxazines, epoxies, oxazolines, oxetanes, and combinations thereof. Of course, more than one comonomer may be used to when polymerizing the non-homopolymer. Non limiting examples of such polymers are described in the *International Cosmetic Ingredient Dictionary and Handbook, Seventh Edition*, The Cosmetic, Toiletry, and Fragrance Association, Inc., Washington, D.C., 1997.

Non limiting examples of suitable cationic polymers include copolymers of vinyl monomers having cationic protonated amine or quaternary ammonium functionalities with comonomers such as acrylamide, methacrylamide, alkyl and dialkyl acrylamides, alkyl and dialkyl methacrylamides, alkyl acrylate, alkyl methacrylate, vinyl caprolactone or vinyl pyrrolidone. The alkyl and dialkyl substituted monomers may have from C1 to C7 alkyl groups, more particularly from C1 to C3 alkyl groups. Other suitable comonomers include vinyl esters, vinyl alcohol (made by hydrolysis of vinyl acetate), maleic anhydride, propylene glycol, and ethylene glycol.

Suitable cationic protonated amino and quaternary ammonium monomers for inclusion in the cationic polymers of the personal care compositions herein, include vinyl compounds substituted with dialkylaminoalkyl(meth)acrylate, monoalkylaminoalkyl(meth)acrylate, trialkyl(meth)acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts. The alkyl portions of these monomers may be C1, C2, or C3 alkyl groups or more. Suitable amine-substituted vinyl monomers for use herein include dialkylaminoalkyl(meth) acrylate and dialkylaminoalkyl(meth)acrylamide, wherein the alkyl groups may be C1-C7 hydrocarbyls, more particularly C1-C3 alkyls.

The cationic polymer also may have one or more functionalized groups having a quaternary ammonium moiety, including functionalized polyethers and/or silicones. These polymers may be desired for imparting desirable sensory qualities like smoothness or conditioning. For example, the quaternary ammonium moiety may have one or more C6-C30 alkyl groups, such as distearyl-dimethyl ammonium; dicetyl-dimethyl ammonium; dimethyl-di(hydrogenated tallow) ammonium; dicetylmethylbenzyl ammonium; dicoco-dimethyl ammonium; dibehenyl-diarachidyl-dimethyl ammonium; hydroxypropyl bis-stearyl ammonium; dibehenyl-dimethyl ammonium; dibehenyl-methylbenzyl ammonium; and dimyristyl-dimethyl ammonium.

Note also is made of the family of cationic polymers bearing the INCI designation polyquaternium (or more simply, PQ). The PQ family of polymers comprise a quaternary ammonium moiety, and many such polymers are known in the art. For example, PQ-1 through -47 of these polymers are listed in the *Official Journal of the European Union, Commission Decision* dated 9 Feb. 2006, 2006/257/EC. Even more polyquaternium polymers are known, and include those presented in Table 1:

TABLE 1

Select polyquaternium polymers

| INCI name | trade name | manufacturer |
|---|---|---|
| PQ-2 | Mirapol ® A-15 | Rhodia (Solvay Group) |
| PQ-4 | Celquat ® L-200 | Akzo Nobel |
| PQ-5 | Merquat ® 5 | Nalco Company |
| PQ-6 | Merquat ® 100 | Nalco Company |
| PQ-7 | Conditioneze ® 7 | Ashland Specialty Ingredients |
| PQ-7 | Merquat ® 550 | Nalco Company |
| PQ-10 | Merquat ® 10 | Nalco Company |
| PQ-11 | Gafquat ® | Ashland Specialty Ingredients |
| PQ-16 | Luviquat ® FC 370 | BASF Corporation |
| PQ-17 | Mirapol ® AD-1 | Rhodia (Solvay Group) |
| PQ-18 | Mirapol ® AZ-1 | Rhodia (Solvay Group) |
| PQ-21 | Abil ® B 9905 | Evonik Industries |
| PQ-22 | Merquat ® 22 | Nalco Company |
| PQ-24 | Quatrisoft ® LM 200 | Dow Chemical Company |
| PQ-28 | Gafquat ® HS-100 | Ashland Specialty Ingredients |
| PQ-37 | Synthalen ® CR | 3V Sigma |
| PQ-39 | Merquat ® Plus 3330 | Nalco Company |
| PQ-44 | Luviquat ® UltraCare | BASF Corporation |
| PQ-46 | Luviquat ® Hold | BASF Corporation |
| PQ-47 | Merquat ® 2001 | Nalco Company |
| PQ-53 | Merquat ® 2003 | Nalco Company |
| PA-55 | Styleze ® W | Ashland Specialty Ingredients |
| PQ-68 | Luviquat ® Supreme | BASF Corporation |
| PQ-69 | AquaStyle ™ 300 | Ashland Specialty Ingredients |
| PQ-86 | Luviquat ® Advanced | BASF Corporation |
| PQ-95 | Polyquart ® Ecoclean | Cognis Corporation (BASF) |

Counted among cationic polymers are polysaccharide polymers, such as cationic cellulose derivatives and cationic starch derivatives. Suitable cationic polysaccharide polymers include those which conform to the formula

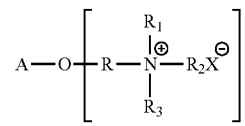

wherein A is an anhydroglucose residual group, such as a starch or cellulose anhydroglucose residual; R is an alkylene, oxyalkylene, polyoxyalkylene, or hydroxyalkylene group, or combination thereof; $R_1$, $R_2$, and $R_3$ independently are alkyl, aryl, alkylaryl, arylalkyl, alkoxyalkyl, or alkoxyaryl groups, each group containing up to and including about 18 carbon atoms, and the total number of carbon atoms for each cationic moiety (i.e., the sum of carbon atoms in $R_1$, $R_2$, and $R_3$) preferably being about 20 or less; and X is an anionic counterion. Suitable cationic cellulose polymers are those polymers available from The Dow Chemical Company in their UCare™ series of polymers, as salts of hydroxy ethyl cellulose reacted with trimethyl ammonium substituted epoxide, (PQ-10). Another suitable cationic cellulose includes the polymeric quaternary ammonium salts of hydroxy ethyl cellulose reacted with lauryl dimethyl ammonium-substituted epoxide, (PQ-24).

Other suitable cationic polymers include guar hydroxypropyltrimonium chloride, sold by Ashland Inc. under the trade name AquaCat™ and N-Hance™. Other suitable cationic polymers include quaternary nitrogen-containing cellulose ethers, some examples of which are described in U.S.

Pat. No. 3,962,418. Other suitable cationic polymers include copolymers of etherified cellulose, guar and starch, some examples of which are described in U.S. Pat. No. 3,958,581.

Another choice for the (B) cationic species is one or more cationic molecules. Included in this category are all molecules containing cationic groups, pseudo-cationic, and/or groups which may be ionized into cationic groups. Examples of cationic molecules to be considered include those comprising primary, secondary, tertiary and/or quaternary amine groups. Specific examples include functionalized silicones having one or more quaternium ammonium moieties and quaterniums. Like their polyquaternium counterparts, many quaterniums are known, including many that find application in the personal care arts. Table 2 presents just a few of the quaterniums that may be used; other known quaterniums also are suitable.

TABLE 2

Select quaterniums

| INCI name | trade name |
|---|---|
| Q-14 | dodecyl(ethyl benzyl)dimethylammonium chloride |
| Q-15 | methenamine 3-chloroallylochloride |
| Q-16 | quaternary ammonium compounds, tris(hydroxyethyl) tallow alkyl, chlorides |
| Q-17 | quaternary ammonium compounds, bis(hydrogenated tallow alkyl)dimethyl, methyl sulfates |
| Q-18 | |
| Q-22 | 3-(D-gluconoylamino)propyl(2-hydroxyethyl)dimethylammonium chloride |
| Q-26 | 1-propanaminium, 3-amino-N-(2-hydroxyethyl)-N,N-dimethyl-, N-mink-oil acyl derivatives, chlorides |
| Q-45 | 3,4-dimethyl-2-[2-(phenylamino)vinyl]oxazolium iodide |
| Q-53 | ethanaminium, 2-amino-N-(2-aminoethyl)-N-[2-[2-(2-hydroxyethoxy)ethoxy]ethyl]-N-methyl-, N,N'-ditallow acyl derivatives, methyl sulfates (salts) |
| Q-87 | imidazolium quat, CAS# 92201-88-2 |

The antiperspiration/deodorant benefits provided by the invention also may be accomplished when the (B) cationic species comprises one or more cations. The cation may carry any number of positive charges, and particularly carries a positive charge from +1 to +4, and more particularly carries a positive charge of +2 or more. The cation(s) may be any simple cation (meaning only one element is involved) or any polyatomic cation (meaning more than one element is involved). Examples of cations for use in the invention include those listed in Table 3.

TABLE 3

Examples of suitable cations.

| cation | non-limiting example(s) |
|---|---|
| aluminum | $Al^{3+}$ |
| ammonium | $NH_4^{1+}$ |
| barium | $Ba^{2+}$ |
| calcium | $Ca^{2+}$ |
| chromium | $Cr^{2+}$, $Cr^{3+}$ |
| cobalt | $Co^{2+}$, $Co^{3+}$ |
| copper | $Cu^{1+}$, $Cu^{2+}$ |
| iron | $Fe^{2+}$, $Fe^{3+}$ |
| hydrogen | $H^+$ |
| hydronium | $H_3O^+$ |
| lithium | $Li^+$ |
| magnesium | $Mg^{2+}$ |
| manganese | $Mn^{2+}$, $Mn^{3+}$ |
| nitronium | $NO_2^{1+}$ |
| potassium | $K^{1+}$ |
| silver | $Ag^{1+}$ |

TABLE 3-continued

Examples of suitable cations.

| cation | non-limiting example(s) |
|---|---|
| sodium | $Na^{1+}$ |
| strontium | $Sr^{2+}$ |
| tin | $Sn^{2+}$, $Sn^{4+}$ |
| zinc | $Zn^{2+}$ |

More broadly, the invention fully embraces the use of these (B) cations (shown in Table 3) in antiperspirant/deodorant compositions absent the (A) polymer having a non-zero acid value. In this aspect, the invention contemplates the antiperspirant efficacy provided by one or more of these cations (either with or without aluminium and/or zirconium cations) in a formula that otherwise resembles known antiperspirant/deodorant compositions. For example, it is possible to reformulate a known antiperspirant/deodorant composition by removing part or even all of the aluminium and/or zirconium cations and replace with one or more of the cations in Table 3. These known antiperspirant/deodorant compositions will contain known ingredients in amounts that are typical in the art.

Due to the cosmetic and/or drug nature of antiperspirant/deodorant compositions, it may be helpful to formulate with cation(s) having low, negligible, or no toxicological effect to the user. Because local jurisdictions make this determination, it is not possible to specify all possibilities them here. Cations that may find use may include the following: aluminium, ammonium, barium, calcium, copper, iron, hydronium, magnesium, manganese, nitronium, potassium, sodium, strontium, zinc, and combinations thereof. More particularly, the cation may include one or more of: aluminium, ammonium, calcium, copper, iron, magnesium, manganese, strontium, or zinc.

The (B) cationic species may be provided in the form of one or more salts, particularly those that are approved for use in cosmetic and/or drug products. Such salts may be formed by the combination of one or more cation(s)/cationic group(s) with one or more anion(s). Examples of anionic groups include those summarized in Table 4, although a knowledgeable chemist can identify more.

TABLE 4

Examples of anions

| anion | symbol |
|---|---|
| acetate | $CH_3COO^{1-}$ |
| amide | $NH_2^{1-}$ |
| bromate | $BrO_3^{1-}$ |
| bromide | $Br^{1-}$ |
| carbonate | $CO_3^{2-}$ |
| chlorate | $ClO_3^{1-}$ |
| chloride | $Cl^{1-}$ |
| chlorite | $ClO_2^{1-}$ |
| chromate | $CrO_4^{2-}$ |
| dichromate | $Cr_2O_7^{2-}$ |
| dihydrogen phosphate | $H_2PO_4^{1-}$ |
| fluoride | $F^{1-}$ |
| formate | $HCOO^{1-}$ |
| gluconate | $C_6H_{11}O_7^{1-}$ |
| hydride | $H^{1-}$ |
| hydrogen carbonate (bicarbonate) | $HCO_3^{1-}$ |
| hydrogen phosphate | $HPO_4^{2-}$ |
| hydrogen sulfate | $HSO_4^{1-}$ |
| hydroxide | $OH^{1-}$ |
| hypobromite | $OBr^{1-}$ |
| hypochlorite | $OCl^{1-}$ |

TABLE 4-continued

Examples of anions

| anion | symbol |
|---|---|
| iodate | $IO_3^{1-}$ |
| iodide | $I^{1-}$ |
| nitrate | $NO_3^{1-}$ |
| nitride | $N^{3-}$ |
| nitrite | $NO_2^{1-}$ |
| oxalate | $C_2O_4^{2-}$ |
| oxide | $O^{2-}$ |
| perchlorate | $ClO_4^{1-}$ |
| permanganate | $MnO_4^{1-}$ |
| peroxide | $O_2^{2-}$ |
| phosphate | $PO_4^{3-}$ |
| sulfate | $SO_4^{2-}$ |
| sulfide | $S^{2-}$ |
| sulfite | $SO_3^{2-}$ |
| thiosulfate | $S_2O_3^{2-}$ |

A fourth choice for the (B) cationic species is one or more cationic carriers. This category includes discrete particles that carry a cationic charge, which may intrinsic to the material or due to modification of the material, e.g., chemical modification of the surface. Contemplated is the use of surface modified silica, talc, clays, and other pigments (or pigment-like materials). The cationic carrier also may be any positively charged encapsulate or microencapsulate of any material, including but not limited to pigments, perfume oils, fragrances, skin conditioners, astringents, biological extracts, humectants, and lubricants. For example, the positively charged encapsulate or microencapsulate material may be one or more natural or synthetic polymers and/or molecules, including, but not limited to those materials described earlier.

Within the second embodiment of the invention, the amounts of the (A) polymer(s) having a non-zero acid value and the (B) cationic specie(s) may be any ratio such that, when combined a composition is produced that reduces perspiration compared to a placebo control that provides no perspiration benefit (i.e., no treatment). In one aspect, the amounts of (A) and (B) may be chosen so that the effective anionic equivalents of the (A) polymer(s) are roughly in proportion with the effective cationic equivalents of the (B) cationic species. The term "effective" refers to equivalents that are actually available for effective antiperspirant control, and includes considerations such as charge equivalents, solubility, compatibility with other ingredients, the composition form, and the delivery device. More particularly, the amounts may range as summarized in Table 5.

TABLE 5

Ranges (A) and (B) ingredients (by weight) according to the second embodiment

| ranges | (A) polymer(s) having a non-zero acid value | | (B) cationic species | |
|---|---|---|---|---|
| | from about: | to about: | from about: | to about: |
| broad: | 0.1% | 15% | 0.1% | 10% |
| middle: | 0.5% | 10% | 0.5% | 7% |
| narrow: | 2% | 2% | 1% | 5% |

In various embodiments it may be advantageous for the antiperspirant/deodorant composition to be substantially anhydrous (i.e., the antiperspirant/deodorant product does not contain more than about 10% water), to be essentially anhydrous (i.e., the antiperspirant/deodorant product does not contain more than about 5% water), to be almost completely anhydrous (i.e., the antiperspirant/deodorant product does not contain more than about 2% water), or even to be anhydrous (i.e., the antiperspirant/deodorant product does not contain more than about 2% water). Antiperspirant/deodorant products that contain zero water may be particularly useful.

Additional Ingredients

As discussed in this section, the antiperspirant/deodorant compositions may include additional ingredient(s) that may assist product manufacturing, delivery, performance, and/or perceived sensory qualities. These additional ingredient(s) typically may be selected from those compounds typically known and used in personal care products, particularly skin care. For convenience, these compounds may be considered to belong to one or more of the following categories: antiperspirant actives, absorbents, deodorant agents, antimicrobials, dyes or colorants, emollients, moisturizers, fragrances, perfumes, volatile oils, emulsifiers, humectants, diluents, bulking agents, distributing agents, rheology agents, glyceride oils, silicas, hair growth inhibitors, pharmaceuticals actives, UV actives, preservatives, surfactants, solvents (particularly non-aqueous solvents), wash-off aids. One skilled in the art recognizes that many of these materials serve multiple purposes. Many times the antiperspirant/deodorant composition will comprise more than one additional ingredient, and may be a blend of multiple additional ingredients.

In one aspect, the optional ingredients include those known in the field of antiperspirants and/or /deodorants, including the disclosures provided by U.S. Patent Application 2010/0322876, U.S. Pat. No. 6,616,921, and international patent application WO 2010/072625. These documents are hereby incorporated in their entirety by reference.

Active antiperspirant active suitable for use in the antiperspirant/deodorant compositions of the present teachings can include any compound, composition or other material having antiperspirant activity. Active antiperspirant ingredients include astringent metallic salts, especially the inorganic salts of aluminum, zirconium, and zinc, as well as their mixtures. Depending on the product form and intended use, aluminum and zirconium salts may be used, such as aluminum halides, aluminum chlorohydrate, aluminum hydroxyhalides, zirconyl oxyhalides, zirconyl hydroxyhalides, and mixtures thereof.

Aluminum salts are typical antiperspirant actives that can be used, particularly those that conform to the formula: $Al_2(OH)_aCl_b \cdot xH_2O$ where a is from about 2 to about 5; the sum of a and b is about 6; y is from about 1 to about 6; and where a, b, and y may have non-integer values. Aluminum chlorohydroxides, also referred to as "basic chlorohydroxide," are one specific illustration of these compounds, for which a is 5, and "⅔ basic chlorohydroxide," for which a is 4.

Zirconium salts for use in the antiperspirant/deodorant compositions include those that described by the formula: $ZrO(OH)_{2-a}Cl_a \cdot xH_2O$, where a is from about 1.1 to about 2.0; y is from about 1 to about 8; and wherein a and y may both have non-integer values. Zirconium salts may additionally contain aluminum and glycine, and are commonly known as "ZAG" complexes. These ZAG complexes contain aluminum chlorohydroxide and zirconyl hydroxy chloride conforming to the above described formulas.

Additional active antiperspirant ingredients that may be included in the formation include: aluminum chloride, aluminum chlorohydrate, aluminum chlorohydrex polyethylene glycol, aluminum chlorohydrex propylene glycol, aluminum dichlorohydrate, aluminum dichlorohydrex polyethylene glycol, aluminum dichlorohydrex propylene glycol, aluminum sesquichlorohydrate, aluminum sesquichlorohydrex polyethylene glycol, aluminum sesquichlorohydrex propylene glycol, and aluminum zirconium octachlorohydrate.

Further information regarding suitable antiperspirant actives include those described in U.S. Pat. No. 6,342,210, which is incorporated in its entirety by reference.

While the antiperspirant/deodorant compositions may or may not comprise aluminium cations nor zirconium cations. Examples of some cations that find application are listed in Table 3. Additionally, one or more antiperspirant actives from natural sources also may be included in the invention's formulations, which or without aluminium cations and/or zirconium cations. The inclusion of antiperspirant actives from natural sources may be an attractive option for all-natural products. These natural actives may be sourced from plant or inorganic material, and include compounds such as: *salvia officinalis* oil, psyllium, sage extract, lavender oil, rosemary oil, tea tree oil, lemon juice, lemon oil, lime juice, lime oil, baking soda (sodium bicarbonate), cornstarch, green clay, coconut oil, witch hazel extract, and oak gall extract.

The antiperspirant/deodorant compositions of the present teachings can be formulated as any known or otherwise effective product form for providing topical application of an active antiperspirant ingredient and/or an active deodorant ingredient to the desired area of the skin. These compositions may be used in the axilla (i.e., arm pit), or on the body (e.g., back, neck, chest, feet, hands) where needed. The product form may be tailored to suit the needs of these application areas. Representative product forms include solid and solid-like forms (e.g., sticks, waxes, powders), liquids (e.g., aerosol sprays, pump sprays, mist sprays, roll-ons, wipes), and semi-solids (e.g., gels, creams, soft solids, lotions). Product forms involving spraying, pumping, and misting may be facilitated by the method disclosed in co-pending international application PCT/US11/31088, which is incorporated in its entirety by reference.

For purposes of maintaining or enhancing antiperspirant/deodorant efficacy, it may be beneficial to separate one or more antiperspirant/deodorant ingredients to prevent their mixing or even to maintain their compatibility. The separation can be effected by maintaining these components in physically separate locations of a package unit or application device prior to use, or by separating them chemically. For example, if the antiperspirant/deodorant composition is in the form of an emulsion, the active antiperspirant ingredient and the water dispersible organic polymer can be in different phases of the composition. Or, one or more ingredients can be encapsulated or microencapsulated to maintain separation inside the product unit, where the encapsulation is then dissolved or eroded upon application and blending. As another example, the (A) polymer having a non-zero acid value and the (B) cationic species can be incorporated into a diluent in which each is insoluble. Upon application, these ingredients may be allowed to mix, as in the blending of.

If the intended product form is an aerosol spray, then one or more propellants may be added to the antiperspirant/deodorant composition to aide in its delivery. The propellant component may contain dimethyl ether or a combination of dimethyl ether and any other known or otherwise suitable propellant for application to the skin, specifically a combination of dimethyl ether and a hydrocarbon propellant. The dimethyl ether or total propellant concentration in the pressurized antiperspirant compositions of the present invention may range from about 5% to about 99%, more specifically from about 15% to about 90%, and even more specifically from about 30% to about 70%, by weight of the composition. The propellants suitable for use in the antiperspirant/deodorant compositions include any hydrocarbon propellant known for or otherwise suitable for application to human skin, non limiting examples of which include propane, butane, pentane, isobutane, and combinations thereof. Suitable examples of hydrocarbon propellants include propellants 22, 142b, and 152a. These propellants are generally in the form of liquefied gases when formulated into the antiperspirant compositions. The composition may comprise other propellants such as nitrous oxide, carbon dioxide, and/or halogenated hydrocarbons, such as trichlorofluoromethane, dichlorodifluoromethane, dichlorotetrafluoroethane trichlorotrifluoroethane, trichlorotetrafluoroethane, monochlorodifluoromethane, and their combinations. The antiperspirant/deodorant products may be stored in and dispensed from a suitable package or applicator device as is known and used in the art.

The antiperspirant/deodorant compositions of the present teachings can be prepared by any known or otherwise effective technique, suitable for providing an antiperspirant/deodorant composition of the desired form and having the essential materials described herein. Many such techniques are described in the antiperspirant/deodorant formulation arts for the described product forms.

Further, the present invention is illustrated in detail by way of the below given examples. The examples are given herein for illustration of the invention and are not intended to be limiting thereof.

EXAMPLES

Example 1

Antiperspirant/Deodorant Stick with Zinc Chloride and Calcium/Sodium PVM/MA Copolymer An antiperspirant/deodorant stick was formulated with the ingredients and proportions shown in Table 6. This formula did not contain any aluminium salt(s), zirconium salt(s), or all-natural antiperspirant active(s) (e.g., plant extracts), any of which could be added as optional ingredient(s) to further enhance antiperspirant efficacy.

TABLE 6

The antiperspirant/deodorant stick (#12155-20) of Example 1.

| ingredient | trade name | supplier | addition level (% w/w) |
|---|---|---|---|
| cyclomethicone | D5 Cyclomethicone | The Scent Works! | 65 |
| polypropylene glycol-14 butyl ether | Arlamol ™ PB14 | Croda International | 2 |
| phenethyl benzoate | X-Tend ™ 226 | Ashland Specialty Ingredients | 1 |
| hydrogenated castor oil | Castrowax MP 80 | Perform. Materials Inc. | 2 |
| polyethylene glycol-100 stearate & glyceryl stearate | Arlacel ™ 165 | Croda International | 1 |
| stearyl alcohol C18 | Lanette ® 18 | Cognis | 20 |
| talc 200 | Imperial 200 | Luzenac | 3 |
| zinc chloride (anhydrous) | | Alfa Aesar | 1 |
| calcium/sodium PVM/MA copolymer | Gantrez ® MS-955 | Ashland Specialty Ingredients | 5 |
| total | | | 100% |

Example 2

Antiperspirant/Deodorant Stick with PVM/MA Decadiene Crosspolymer

An antiperspirant/deodorant stick was formulated with the ingredients and proportions shown in Table 7. This formula did not contain any aluminium salt(s), zirconium salt(s), or all-natural antiperspirant active(s) (e.g., plant extracts), any of which could be added as optional ingredient(s) to further enhance antiperspirant efficacy.

TABLE 7

The antiperspirant/deodorant stick (#12155-26) of Example 2.

| ingredient | trade name | supplier | addition level (% w/w) |
|---|---|---|---|
| cyclomethicone | D5 Cyclomethicone | The Scent Works! | 66 |
| polypropylene glycol-14 butyl ether | Arlamol ™ PB14 | Croda International | 2 |
| phenethyl benzoate | X-Tend ™ 226 | Ashland Specialty Ingredients | 1 |
| hydrogenated castor oil | Castrowax MP 80 | Perform. Materials Inc. | 2 |
| polyethylene glycol-100 stearate & glyceryl stearate | Arlacel ™ 165 | Croda International | 1 |
| stearyl alcohol C18 | Lanette ® 18 | Cognis | 20 |
| talc 200 | Imperial 200 | Luzenac | 3 |
| PVM/MA decadiene crosspolymer | AP-1 | Ashland Specialty Ingredients | 5 |
| total | | | 100% |

Example 3

Antiperspirant/Deodorant Stick with PVP/DMAPA Acrylates Copolymer and Calcium/Sodium PVM/MA Copolymer An antiperspirant/deodorant stick was formulated with the ingredients and proportions shown in Table 8. This formula did not contain any aluminium salt(s), zirconium salt(s), or all-natural antiperspirant active(s) (e.g., plant extracts), any of which could be added as optional ingredient(s) to further enhance antiperspirant efficacy.

TABLE 8

The antiperspirant/deodorant stick (#12155-35) of Example 3.

| ingredient | trade name | supplier | addition level (% w/w) |
|---|---|---|---|
| cyclomethicone | D5 Cyclomethicone | The Scent Works! | 67 |
| polypropylene glycol-14 butyl ether | Arlamol ™ PB14 | Croda International | 2 |
| phenethyl benzoate | X-Tend ™ 226 | Ashland Specialty Ingredients | 1 |
| hydrogenated castor oil | Castrowax MP 80 | Perform. Materials Inc. | 2 |
| polyethylene glycol-100 stearate & glyceryl stearate | Arlacel ™ 165 | Croda International | 1 |
| stearyl alcohol C18 | Lanette ® 18 | Cognis | 20 |
| talc 200 | Imperial 200 | Luzenac | 3 |
| PVP/DMAPA acrylates copolymer | Styleze ® CC-10 | Ashland Specialty Ingredients | 2 |
| calcium/sodium PVM/MA copolymer | Gantrez ® MS-955 | Ashland Specialty Ingredients | 2 |
| total | | | 100% |

Example 4

Antiperspirant/Deodorant Stick with Polyquaternium-28 and Calcium/Sodium PVM/MA Copolymer An antiperspirant/deodorant stick was formulated with the ingredients and proportions shown in Table 9. This formula did not contain any aluminium salt(s), zirconium salt(s), or all-natural antiperspirant active(s) (e.g., plant extracts), any of which could be added as optional ingredient(s) to further enhance antiperspirant efficacy.

TABLE 9

The antiperspirant/deodorant stick (#12155-36) of Example 4.

| ingredient | trade name | supplier | addition level (% w/w) |
|---|---|---|---|
| cyclomethicone | D5 Cyclomethicone | The Scent Works! | 67 |
| polypropylene glycol-14 butyl ether | Arlamol ™ PB14 | Croda International | 2 |
| phenethyl benzoate | X-Tend ™ 226 | Ashland Specialty Ingredients | 1 |
| hydrogenated castor oil | Castrowax MP 80 | Perform. Materials Inc. | 2 |
| polyethylene glycol-100 stearate & glyceryl stearate | Arlacel ™ 165 | Croda International | 1 |
| stearyl alcohol C-18 | Lanette ® 18 | Cognis | 20 |
| talc 200 | Imperial 200 | Luzenac | 3 |
| polyquaternium-28 (VP/methacryl-amidopropyl trimethylammonium chloride) | Conditioneze ® NT-20 | Ashland Specialty Ingredients | 2 |
| calcium/sodium PVM/MA copolymer | Gantrez ® MS-955 | Ashland Specialty Ingredients | 2 |
| total | | | 100% |

Example 5

Antiperspirant/Deodorant Stick with Zinc Gluconate and Calcium/Sodium PVM/MA Copolymer An antiperspirant/deodorant stick is formulated with the ingredients and proportions shown in Table 10. This formula does not contain any aluminium salt(s), zirconium salt(s), or all-natural antiperspirant active(s) (e.g., plant extracts), any of which can be added as optional ingredient(s) to further enhance antiperspirant efficacy.

TABLE 10

The antiperspirant/deodorant stick (#11916-139) of Example 5.

| ingredient | trade name | supplier | addition level (% w/w) |
|---|---|---|---|
| cyclomethicone | D5 Cyclomethicone | The Scent Works! | 61 |
| polyethylene glycol-100 stearate & glyceryl stearate | Arlacel ™ 165 | Croda International | 1 |
| phenethyl benzoate | X-Tend ™ 226 | Ashland Specialty Ingredients | 1 |
| hydrogenated castor oil | Castrowax MP 80 | Perform. Materials Inc. | 2 |
| stearyl alcohol C-18 | Lanette ® 18 | Cognis | 20 |
| talc 200 | Imperial 200 | Luzenac | 3 |
| polypropylene glycol-14 butyl ether | Arlamol ™ PB14 | Croda International | 2 |
| zinc gluconate | | Sigma-Aldrich Co. LLC | 5 |
| calcium/sodium PVM/MA copolymer | Gantrez ® MS-955 | Ashland Specialty Ingredients | 5 |
| total | | | 100% |

Example 6

Antiperspirant/Deodorant Stick with Copper (II) Sulfate and Calcium/Sodium PVM/MA Copolymer An antiperspirant/deodorant stick is formulated with the ingredients and proportions shown in Table 11. This formula does not contain any aluminium salt(s), zirconium salt(s), or all-natural antiperspirant active(s) (e.g., plant extracts), any of which can be added as optional ingredient(s) to further enhance antiperspirant efficacy.

TABLE 11

The antiperspirant/deodorant stick (#11916-140) of Example 6.

| ingredient | trade name | supplier | addition level (% w/w) |
|---|---|---|---|
| cyclomethicone | D5 Cyclomethicone | The Scent Works! | 61 |
| polyethylene glycol-100 stearate & glyceryl stearate | Arlacel ™ 165 | Croda International | 1 |
| phenethyl benzoate | X-Tend ™ 226 | Ashland Specialty Ingredients | 1 |
| hydrogenated castor oil | Castrowax MP 80 | Perform. Materials Inc. | 2 |
| stearyl alcohol C-18 | Lanette ® 18 | Cognis | 20 |
| talc 200 | Imperial 200 | Luzenac | 3 |
| polypropylene glycol-14 butyl ether | Arlamol ™ PB14 | Croda International | 2 |
| copper (II) sulfate | | Sigma-Aldrich Co. LLC | 5 |
| calcium/sodium PVM/MA copolymer | Gantrez ® MS-955 | Ashland Specialty Ingredients | 5 |
| total | | | 100% |

Example 7

Antiperspirant/Deodorant Aerosol with PVM/MA Decadiene Crosspolymer

An antiperspirant/deodorant concentrate aerosol spray is formulated with the ingredients and proportions shown in Table 12. This formula does not contain any aluminium salt(s), zirconium salt(s), or all-natural antiperspirant active(s) (e.g., plant extracts), any of which can be added as optional ingredient(s) to further enhance antiperspirant efficacy.

This concentrate is prepared into a finished formula that contains 40 parts (w/w) of the concentrate and 60 parts (w/w) of a suitable aerosol propellant, such as hydrocarbons, dimethyl ether, fluorocarbons.

TABLE 12

The antiperspirant/deodorant stick (#11916-141-1) of Example 7.

| ingredient | trade name | supplier | addition level (% w/w) |
|---|---|---|---|
| cyclomethicone | D5 Cyclomethicone | The Scent Works! | 45 |
| diisopropyl adipate | Ceraphyl ® 230 | Ashland Specialty Ingredients | 37.5 |
| phenethyl benzoate | X-Tend ™ 226 | Ashland Specialty Ingredients | 5 |
| organically modified hectorite | Bentone 38-V | Elementis Specialties | 2.5 |
| Propylene carbonate | Jeffsol ® | Huntsman Corporation | 5 |
| PVM/MA decadiene crosspolymer | AP-1 | Ashland Specialty Ingredients | 5 |
| total | | | 100% |

Example 8

Antiperspirant/Deodorant Roll-On with PVM/MA Decadiene Crosspolymer

An antiperspirant/deodorant concentrate aerosol spray is formulated with the ingredients and proportions shown in Table 13. This formula does not contain any aluminium salt(s), zirconium salt(s), or all-natural antiperspirant active(s) (e.g., plant extracts), any of which can be added as optional ingredient(s) to further enhance antiperspirant efficacy.

This concentrate can be prepared into a finished formula by taking 40 parts (w/w) of the concentrate and 60 parts (w/w) of a suitable aerosol propellant.

TABLE 13

The antiperspirant/deodorant stick (#11916-141-1) of Example 8.

| ingredient | trade name | supplier | addition level (% w/w) |
|---|---|---|---|
| cyclopentasiloxane | Si-Tec ™ CM 040 | Ashland Specialty Ingredients | 90 |
| organically modified hectorite | Bentone 38-V | Elementis Specialties | 3 |
| propylene carbonate | Jeffsol ® | Huntsman Corporation | 1 |
| ethanol (200 proof) | | | 1 |
| PVM/MA decadiene crosspolymer | AP-1 | Ashland Specialty Ingredients | 5 |
| total | | | 100% |

Example 9

Clinical Evaluation of Antiperspirant/Deodorant Formulas

The formulas of Example 1 and 2 were tested in separate clinical trials to determine their effectiveness in reducing perspiration. The two studies were conducted using a modified procedure defined by the Food and Drug Administration (FDA) Guidelines For Effectiveness Testing Of OTC Antiperspirant Drug Products in accordance with §350.60 of the Final Monograph entitled "Antiperspirant Drug Products For Over the Counter Human Use," Final Rule, 21 CFR Parts 310, 350 and 369 (Federal Register, 64, 110, Monday, Jun. 9, 2003). In each trial a cohort of five healthy women was studied under the supervision of qualified medical staff. All volunteers were required to complete a 17-day pretreatment conditioning period, during which both axillae were washed using Ivory® soap, and antiperspirant/deodorant products were not used. A single application of the test product was uniformly applied in one axillary vault by trained technicians, while the other served as a placebo (untreated) control. After 24 hours, sweating was stimulated by placing the volunteers in a controlled environment at 100° F. (37.8° C.) and 35% RH. Quantitative measurements of sweat were made by placing non-woven, cotton padding fabric in the axillae for two 20-minute periods, and then the padding was weighed. The ratio of test axilla perspiration to control axilla perspiration, adjusted for the ratio of right-to-left axillary sweating rate, was defined for each subject by the formula:

$$Z = \frac{PC \times T}{PT \times C}$$

where Z is the adjusted perspiration ratio, PC is the pretreatment measure of moisture for the placebo controlled axilla, PT is the pretreatment measure for the test axilla, T is the treated measure for the test axilla, and C is the corresponding quantity for the placebo controlled axilla. Mean and median values were calculated to measure the central tendency of the adjusted perspiration ratio (Z) values.

The mean and median sweat reductions due to the formulas according to the invention are shown in Table 14. These results show that the antiperspirant/deodorant compositions were effective in reducing perspiration.

TABLE 14

Clinical trial results examining the antiperspirant/deodorant compositions of Examples 1 and 2.

| AP/DEO formula | AP active | sweat reduction due to AP/DEO formula treatment | |
|---|---|---|---|
| | | mean | median |
| Example 1 | calcium/sodium PVM/MA copolymer (Gantrez® MS-955) | 20.55% | 20.70% |
| Example 2 | PVM/MA decadiene crosspolymer (AP-1) | 19.26% | 18.95% |

While this invention has been described in detail with reference to certain preferred embodiments, it should be appreciated that the present invention is not limited to those precise embodiments. Rather, in view of the present disclosure, which describes the current best mode for practicing the invention, many modifications and variations would present themselves to those skilled in the art without departing from the scope and spirit of this invention.

We claim:

1. A method for treating body perspiration and/or body odors associated with said perspiration, comprising an application to the skin surface an effective amount of an antiperspirant/deodorant composition comprising at least one polymer selected from the group consisting of PVM/MA copolymer, crosslinked PVM/MA copolymer, PVM/MA decadiene crosspolymer, IB/MA copolymer, and combinations thereof as the sole active antiperspirant/deodorant species, wherein said composition is essentially free of aluminum cations or zirconium cations.

2. The method according to claim 1, wherein the composition has from 0.1% (w/w) to 15% (w/w) of said polymer.

3. The method according to claim 1 wherein the percentage of perspiration reduction provided by said composition is greater than a placebo control absent said polymer, aluminum cations, and zirconium cations.

4. The method according to claim 1, wherein the composition further comprises: an additional ingredient selected from the group consisting of absorbent, agent, antimicrobial, dye or colorant, emollient, moisturizer, fragrance, perfume, volatile oil, emulsifier, humectant, diluent, bulking agent, distributing agents, rheology agent, glyceride oil, silica, hair growth inhibitor, pharmaceutical active, UV active, preservative, surfactant, solvent, wash-off aid, and combinations thereof.

5. The method according to claim 1, wherein the composition has the form of a stick, wax, powder, aerosol spray, pump spray, mist spray, roll-on, wipe, gel, cream, soft solid, or lotion.

* * * * *